United States Patent
Geric et al.

(10) Patent No.: US 11,583,347 B2
(45) Date of Patent: Feb. 21, 2023

(54) HEART-LUNG MACHINE WITH AUGMENTED REALITY DISPLAY

(71) Applicant: Terumo Cardiovascular Systems Corporation, Ann Arbor, MI (US)

(72) Inventors: Joseph Geric, Livonia, MI (US); Takeshi Tsubouchi, Dexter, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 147 days.

(21) Appl. No.: 17/085,765

(22) Filed: Oct. 30, 2020

(65) Prior Publication Data

US 2021/0128254 A1 May 6, 2021

Related U.S. Application Data

(60) Provisional application No. 62/928,773, filed on Oct. 31, 2019.

(51) Int. Cl.
*A61B 34/00* (2016.01)
*A61B 90/50* (2016.01)
*A61B 90/00* (2016.01)
*G02B 27/01* (2006.01)

(52) U.S. Cl.
CPC .............. *A61B 34/25* (2016.02); *A61B 90/37* (2016.02); *A61B 90/50* (2016.02); *G02B 27/0172* (2013.01); *A61B 2090/365* (2016.02); *A61B 2090/372* (2016.02); *A61B 2090/502* (2016.02)

(58) Field of Classification Search
CPC ......... A61B 34/25; A61B 90/37; A61B 90/50; A61B 2090/365; A61B 2090/372; A61B 2090/502; G02B 27/0172
USPC ........................................................ 600/424
See application file for complete search history.

(56) References Cited

U.S. PATENT DOCUMENTS

| | | | |
|---|---|---|---|
| 4,182,504 A | 1/1980 | Bernhard | |
| 4,626,980 A | 12/1986 | McGuire | |
| 4,708,714 A * | 11/1987 | Larsson | A61M 1/3486 604/6.06 |
| 6,383,767 B1 | 5/2002 | Polak | |

(Continued)

FOREIGN PATENT DOCUMENTS

| CN | 2650428 | 10/2004 |
|---|---|---|
| CN | 2650428 Y * | 10/2004 |

(Continued)

OTHER PUBLICATIONS

PCT International Search Report and Written Opinion in International Appln. No. PCT/US2020/058267, dated Dec. 22, 2020, 13 pages.

(Continued)

*Primary Examiner* — Mark Edwards
(74) *Attorney, Agent, or Firm* — Fish & Richardson P.C.

(57) ABSTRACT

This document describes devices used during surgical procedures for the treatment of heart conditions. For example, this document describes technology to monitor the operations of a heart-lung machine and then shows associated read outs on a head-worn display in order to provide an augmented-reality presentation. For example, various sensors on and around a heart-lung machine, patient, and/or extracorporeal circuit can monitor the operations of the procedure using the heart-lung machine.

19 Claims, 6 Drawing Sheets

(56) References Cited

U.S. PATENT DOCUMENTS

| | | |
|---|---|---|
| 6,454,710 B1 | 9/2002 | Ballerstady et al. |
| 6,630,805 B2 | 10/2003 | Makaran |
| 6,664,750 B2 | 12/2003 | Pelonis |
| 7,521,019 B2 | 4/2009 | Polak et al. |
| 7,613,504 B2 | 11/2009 | Rowe |
| 7,774,044 B2 | 8/2010 | Sauer et al. |
| 8,216,854 B2 | 7/2012 | Ballerstady et al. |
| 8,409,877 B2 | 4/2013 | Liu et al. |
| 8,814,691 B2 | 8/2014 | Haddick et al. |
| 9,276,063 B2 | 3/2016 | Zhang et al. |
| 9,309,550 B2 | 4/2016 | Cooper et al. |
| 9,625,456 B2 | 4/2017 | Bradbury et al. |
| 9,901,295 B2 | 2/2018 | Iverson et al. |
| 10,013,808 B2 | 7/2018 | Jones et al. |
| 10,180,572 B2 | 1/2019 | Osterhout et al. |
| 10,197,803 B2 | 2/2019 | Badiali et al. |
| 10,250,838 B1* | 4/2019 | Herz ................. H04N 21/4316 |
| 11,158,126 B1* | 10/2021 | Petrov ..................... G06F 3/012 |
| 2002/0160520 A1 | 10/2002 | Ofloff et al. |
| 2005/0027176 A1 | 2/2005 | Xie |
| 2005/0148100 A1 | 7/2005 | Su et al. |
| 2007/0015999 A1 | 1/2007 | Heldreth et al. |
| 2007/0052683 A1* | 3/2007 | Knott ..................... G06F 3/1446 |
| | | 345/173 |
| 2007/0208243 A1 | 9/2007 | Gabriel et al. |
| 2008/0039816 A1 | 2/2008 | Svarovsky et al. |
| 2009/0118605 A1 | 5/2009 | Van Duyne et al. |
| 2010/0254911 A1 | 10/2010 | Sharma et al. |
| 2011/0275985 A1 | 11/2011 | Lowery, Jr. et al. |
| 2013/0197327 A1 | 8/2013 | Chen et al. |
| 2013/0278631 A1 | 10/2013 | Border et al. |
| 2014/0246624 A1 | 9/2014 | Seubert et al. |
| 2015/0002374 A1 | 1/2015 | Erinjippurath et al. |
| 2015/0212577 A1* | 7/2015 | Hotta ...................... G06F 3/005 |
| | | 345/156 |
| 2015/0261920 A1* | 9/2015 | Blick ..................... G16H 15/00 |
| | | 705/3 |
| 2016/0243262 A1 | 8/2016 | Ortac et al. |
| 2017/0103440 A1 | 4/2017 | Xing et al. |
| 2017/0160549 A1 | 6/2017 | Badiali et al. |
| 2017/0173262 A1 | 6/2017 | Veltz |
| 2017/0202633 A1 | 7/2017 | Liu |
| 2017/0212124 A1 | 7/2017 | Thalhammer et al. |
| 2017/0340225 A1 | 11/2017 | Ulmer et al. |
| 2018/0000321 A1 | 1/2018 | Wales et al. |
| 2018/0082480 A1 | 3/2018 | White et al. |
| 2018/0147113 A1 | 5/2018 | Dellimore et al. |
| 2018/0322702 A1 | 11/2018 | Djajadiningrat |
| 2019/0001127 A1* | 1/2019 | Evans .................... A61H 31/00 |
| 2019/0064520 A1* | 2/2019 | Christensen ........... G16H 40/63 |
| 2019/0183576 A1 | 6/2019 | Fahim et al. |
| 2020/0330675 A1* | 10/2020 | Wolfgramm ........ A61M 1/3666 |

FOREIGN PATENT DOCUMENTS

| | | |
|---|---|---|
| EP | 0562742 | 9/1993 |
| EP | 0952433 | 2/2008 |
| EP | 3511036 | 7/2019 |
| WO | WO 2003/042968 | 5/2003 |
| WO | WO 2017/214047 | 12/2017 |
| WO | WO 2019/137677 | 7/2019 |

OTHER PUBLICATIONS

PCT International Preliminary Report on Patentability in International Appln. No. PCT/US2020/058267, dated May 3, 2022, 11 pages.

Extended European Search Report in European Appln No. 20882706.3, dated Nov. 24, 2022, 8 pages.

\* cited by examiner

HEART-LUNG MACHINE WITH AUGMENTED REALITY DISPLAY

CROSS-REFERENCE TO RELATED APPLICATIONS

This application claims the benefit of U.S. Provisional Application Ser. No. 62/928,773, filed Oct. 31, 2019. The disclosure of the prior application is considered part of (and is incorporated by reference in) the disclosure of this application.

BACKGROUND

1. Technical Field

This document relates to a heart-lung machine that provides sensor data to a user in an augmented reality presentation.

2. Background Information

Hollow fiber oxygenators are utilized within the extracorporeal circuit to meet a patient's gas exchange needs during medical procedures such as cardiopulmonary bypass surgery. Blood from the patient is either gravity drained, or VAVD (vacuum assisted venous drainage) is used to obtain the required amount of flow to maintain sufficient volume in a reservoir. A pump, such as a peristaltic pump or a centrifugal pump coupled with a magnetic drive system, is sometimes used in the main line of the circuit in order to pump blood from the reservoir, through the oxygenator, and finally back to the patient.

Augmented reality (AR) is an interactive experience of a real-world environment where the objects that reside in the real-world are enhanced by computer-generated perceptual information, sometimes across multiple sensory modalities, including visual, auditory, haptic, somatosensory and olfactory. The overlaid sensory information can be constructive (i.e., additive to the natural environment), or destructive (i.e., masking of the natural environment).

SUMMARY

In one aspect, this disclosure is directed to a system for displaying heart-lung machine sensor data in augmented reality. The system includes a head-worn augmented-reality display comprising a viewfield through which a user of the augmented-reality display can view physical objects in their field of view, the augmented-reality display configured to render glyphs and to render video in the viewfield such that, as the user views physical objects in their field of view, the user is shown a display of the glyphs and the video as an overlay to the view of the physical objects. The system includes a heart-lung machine configured to engage in an operation to provide a patient with an extracorporeal blood flow circuit. The system includes at least one fine-grain sensor configured to sense a first parameter of the operation of the heart-lung machine. The system includes at least one coarse-grain sensor configured to sense a second parameter of the operation of the heart-lung machine. The system includes at least one video sensor to capture video data of the operation of the heart-lung machine. The system includes a controller comprising a hardware processor and computer memory. The system includes a data-network that communicably couples at least the fine-grain sensor and the coarse-grain sensor to the controller and further couples at least the controller to the head-worn augmented-reality display. The controller is configured to receive, through the data-network, the first parameter of the operation of the heart-lung machine; receive, through the data-network, the second parameter of the operation of the heart-lung machine; receive, through the data-network, the video data of the operation of the heart-lung machine; send, to the augmented-reality display, instructions to show as a glyph an alpha-numeric value based on the first parameter of the operation of the heart-lung machine; send, to the augmented-reality display, instructions to show as a glyph, selected graphic from a plurality of possible graphics based on the second parameter of the operation of the heart-lung machine; and send, to the augmented-reality display, instructions to show a video based on the video data. Other systems, method, devices, products, and software can be used.

Implementations can include some, all, or none of the following features. The coarse-grain sensor is configured to sense the second parameter by sensing a particular physical phenomena; and the video sensor captures video data by capturing the particular physical phenomena. The coarse-grain sensor is a level-sensor configured to sense a level of blood in a reservoir of the heart-lung machine; and the video sensor captures video data of depicting the level of blood in the reservoir of the heart-lung machine. The fine-grain sensor is configured to sense the first parameter by sensing a particular physical phenomena; and the video sensor captures video data by capturing the particular physical phenomena. The coarse-grain sensor is a line pressure sensor configured to sense a pressure in a line of a heart-lung machine; and the video sensor captures video data of depicting the level of blood in a reservoir of the heart-lung machine. The coarse-grain sensor is an air detection sensor configured to sense a presence of air in a line of a heart-lung machine; and the video sensor captures video data of depicting the level of blood in a reservoir of the heart-lung machine. The coarse-grain sensor is an arterial pressure sensor configured to sense a mean arterial pressure of a heart-lung machine; and the video sensor captures video data of depicting the level of blood in a reservoir of the heart-lung machine. The coarse-grain sensor is a flow volume sensor configured to sense a flow volume of a heart-lung machine; and the video sensor captures video data of depicting the level of blood in a reservoir of the heart-lung machine. The coarse-grain sensor is a venous saturation sensor configured to sense a mean venous saturation of a heart-lung machine; and the video sensor captures video data of depicting the level of blood in a reservoir of the heart-lung machine. The plurality of possible graphics includes an altered-graphic that corresponds to the selected graphic and differs from the selected graphic in at least a color. The color is a red color; and the controller is configured to send the selected graphic when the second parameter is within a normal range and to send the altered graphic when the second parameter is outside of a normal range. The controller is configured to send the selected graphic at a first time and to send the altered graphic at a second time later than the first time. The system further comprising a stand-alone monitor; and the controller is further configured to send, to the stand-alone monitor, instructions to show monitor-data on the stand-alone monitor, at least some of the monitor-data including one of the group consisting of the alpha-numeric value, the selected graphic, and the video. The video sensor records an alphanumerical display; and wherein the controller is further configured to generate a corresponding computer-readable value; and send, to the augmented-reality display, instructions to show the corresponding computer-readable value. The controller is further configured to: determine a change to the corresponding computer-readable value; and send, to the augmented-reality display, instructions to show the change to the corresponding computer-readable value. The controller is further configured to determine a change to the second parameter; and send, to the augmented-reality display, instructions to show as a second glyph based on the change of the second parameter. The augmented-reality display comprises light emitters configured to emit light into a transparent viewfield to render the glyphs. The augmented-reality display comprises light emitters configured to emit light into a half mirror viewfield to render the glyphs. The augmented-reality display comprises one or more screens configured to display video to render the glyphs. The augmented-reality display comprises a retinal projector configured to project an image onto one or more eyes of the user to render the glyphs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The technology described in this document can be used to provide one or more benefits. For example, the technology of medical interventions can be improved. A heart-lung machine can be created that provides a perfusionist, or any other user including other clinicians, with an augmented reality monitor that provides an overlay with critical information about the operation of a heart-lung machine that is being used to provide a medical intervention to a patient. The augmented reality monitor may be head-worn, which can allow the perfusionist to move their gaze away from the heart-lung machine while still maintaining awareness of key metrics and sensor readings that need essentially constant monitoring and/or swift reactions. This can allow the perfusionist greater physical mobility, faster response to critical incidents, and superior presentation of data. For example, since a particular reading will always be in a particular location of the perfusionist's view, they may develop skills to look to this part of their view and ascertain information faster than on a fixed screen, which can be in different places relative to the perfusionist based on where the perfusionist is standing, sifting, or moving around the operating room (away from the heart-lung machine).

Swift response by a perfusionist may become very important in any number of critical conditions. As will be understood, patient survival can often depended on what the perfusionist sees and how effectively the perfusionist can respond to the event. As such, the technology described in this document can lead to better patient outcomes, including survival, by enhancing the technology used by the perfusionist or other care provider. In some cases, features of a heart lung machine may change very quickly, for example blood level in a reservoir may quickly drain, which can result in air being introduced into a patient's body. Use of this technology can warn a perfusionist before such a dangerous event.

In addition, the technology described in this document can provide a perfusionist with different kinds of displays based on the kinds of sensing that is available. For fine grain sensors, computer-generated numbers and letters can be generated. However, when fine grain sensors are not available, other next-best options can be used. For example, for coarse grain sensors.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes devices used during surgical procedures for the treatment of heart conditions. For example, this document describes technology to monitor the operations of a heart-lung machine and then shows associated read outs on a head-worn display in order to provide an augmented-reality presentation. For example, various sensors on and around a heart-lung machine, patient, and/or extracorporeal circuit can monitor the operations of the procedure using the heart-lung machine. Then, a controller can generate presentations to be shown (e.g., if an oxygen saturation of 79.9845% is sensed, alpha-numeric characters "8", "0", ".", "0" and "%" can be used). The head-worn display can then render this presentation (e.g., glyphs and video).

Figure 1:
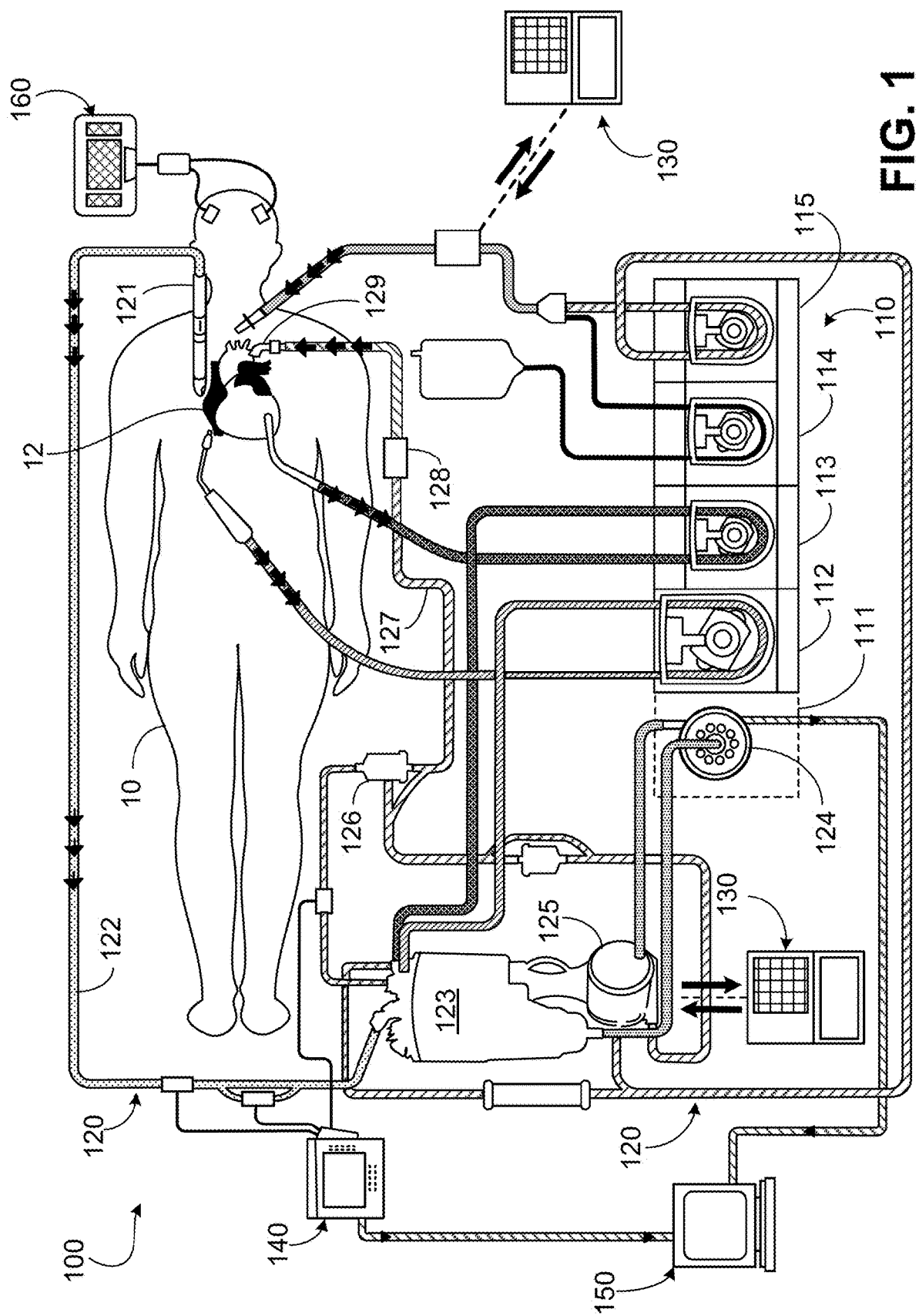
FIG. 1 is a schematic diagram of patient undergoing open-heart surgery while being supported using an extracorporeal circuit in accordance with some embodiments provided herein.

As shown in FIG. 1, various types of medical procedures can be performed on a patient 10 while the patient 10 is connected to a life-sustaining heart/lung bypass machine system 100. In this example, the patient 10 is undergoing open-heart surgery during which the heart 12 and lungs of the patient 10 are temporarily intentionally caused to cease functioning. Because the body of the patient 10 continues to have a metabolic need to receive a supply of circulating oxygenated blood during the medical procedure, however, the heart/lung bypass machine system 100 performs such functions. That is, as described further below, the heart/lung bypass machine system 100 is connected to the patient 10 and performs the functions of the heart 12 and lungs of the patient 10 so that the patient 10 stays alive and healthy during open-heart surgery. The heart/lung bypass machine system 100 can be used for many different types of medical procedures. For example, the medical procedures for which the heart/lung bypass machine system 100 can be used include, but are not limited to, coronary artery bypass grafts, heart valve repairs, heart valve replacements, heart transplants, lung transplants, ablation procedures, repair of septal defects, repair of congenital heart defects, repair of aneurysms, pulmonary endarterectomy, pulmonary thrombectomy, and the like.

The heart/lung bypass machine system 100 is typically set up and operated by a specially-trained clinician called a perfusionist. Perfusionists form part of the wider cardiovascular surgical team that includes cardiac surgeons, anesthesiologists, and nurses. During medical procedures using the heart/lung bypass machine system 100, the perfusionist is tasked with many responsibilities, not the least of which is ensuring that the patient 10 is kept alive and healthy by operating the heart/lung bypass machine system 100 in a manner that maintains blood flow to the patient's tissues, and which regulates levels of oxygen and carbon dioxide in the blood of the patient 10. Other responsibilities of the perfusionist include, but are not limited to, administering blood products, administering anesthetic agents or drugs, measuring selected laboratory values (such as blood cell count), monitoring circulation, monitoring blood gases, surveilling anticoagulation, induction of hypothermia, and hemodilution. The responsibilities of the perfusionist are diverse, dynamic, and critically important to achieving successful outcomes of procedures performed on the patient 10 using the heart/lung bypass machine system 100.

In the depicted example, the heart/lung bypass machine system 100 includes components and sub-systems such as a heart/lung machine 110, an extracorporeal circuit 120, one or more temperature control systems 130, a blood monitoring system 140, a perfusion data management system 150, and a regional oximetry system 160. Some types of procedures that use the heart/lung bypass machine system 100 may not require all of the components and sub-systems that are shown. Some types of procedures that use the heart/lung bypass machine system 100 may require additional components and/or sub-systems that are not shown.

The extracorporeal circuit 120 is connected to the patient 10, and to the heart/lung machine 110. Other systems, such as the temperature control system 130, blood monitoring system 140, and perfusion data management system 150 may also be arranged to interface with the extracorporeal circuit 120. The extracorporeal circuit 120 is connected to the patient 10 at the patient's heart 12. Oxygen-depleted blood (venous blood) from the patient 10 is extracted from the patient 10 at the patient's heart 12 using a venous catheter 121. As described further below, the blood is circulated through the extracorporeal circuit 120 to receive oxygen and remove carbon dioxide. The oxygenated blood is then returned through the extracorporeal circuit 120 to the patient's heart 12 via an aortic cannula 129.

The extracorporeal circuit 120 can include, at least, a venous tube 122 that is coupled to the venous catheter 121, a blood reservoir 123, a centrifugal pump 124, an oxygenator 125, an arterial filter 126, one or more air bubble detectors 128, and an arterial tube 127 that is coupled to the aortic cannula 129. The venous catheter 121 and venous tube 122 are in fluid communication with the venous side of the circulatory system of the patient 10. The venous tube 122 is also in fluid communication with an inlet to the reservoir 123. An outlet from the reservoir 123 is connected by tubing to an inlet of the pump 124. The outlet of the pump 124 is connected by tubing to an inlet of the oxygenator 125. The outlet of the oxygenator 125 is connected by tubing to an inlet of the arterial filter 126. An outlet of the arterial filter 126 is connected to the arterial tube 127. One or more pressure transducers can be located along the arterial tube 127 to detect a heart/lung machine (HLM) system line pressure of the blood in the arterial tube 127, which is measured by the heart/lung machine 110 and monitored by the perfusionist. The arterial tube 127 is connected to the arterial cannula 129, which is in physical contact with the heart 12 and in fluid communication with the arterial side of the circulatory system of the patient 10.

Briefly, the extracorporeal circuit 120 operates by removing venous, oxygen-depleted blood from the patient 10 via the venous catheter 121, and depositing the venous blood in the reservoir 123 via the venous tube 122. In some cases, gravity is used to cause the blood to flow or drain from the patient 10 to the reservoir 123. In some cases, vacuum is used to assist the blood to flow from the patient 10 to the reservoir 123. At least some amount of blood is intended to be maintained in the reservoir 123 at all times during the surgical procedure. Otherwise, if the reservoir 123 becomes empty, air could be pumped into the extracorporeal circuit 120, and potentially into the vasculature of the patient 10. Such a result would likely be catastrophic for the patient 10. Accordingly, the perfusionist is tasked with visually monitoring the level of the blood in the reservoir 123. In addition, level detectors can be included in conjunction with the reservoir 123 to issue an alarm in response to detection of low-level conditions within the reservoir 123. Moreover, one or more air bubble detectors 128 can be located at various sites along the extracorporeal circuit 120. Blood from the reservoir 123 is drawn from the reservoir 123 by the pump 124. While the depicted embodiment includes a one-time use centrifugal pump as the pump 124, in some cases a peristaltic pump of the heart/lung machine 110 is used instead. The pressure generated by the pump 124 propels the blood through the oxygenator 125. The perfusionist will adjust the pump 124 to operate as desired, while avoiding operational issues such as negative cavitation that could create micro air in the blood of the extracorporeal circuit 120. In the oxygenator 125, the venous blood is enriched with oxygen, and carbon dioxide is removed from the blood. The now oxygen-rich arterial blood exits the oxygenator 125, travels through the arterial filter 126 to remove emboli, and is injected into the patient's heart 12 through the arterial tube 160 via the aortic cannula 129. The extracorporeal circuit 120 can also include tubing and other components for facilitating functions such as, but not limited to, drainage of blood accumulating in the heart of the patient 10, providing surgical suction for maintaining visibility of the surgical field, delivery of cardioplegia solution to the heart 12 of the patient 10 during the procedure, measuring blood parameters, removing air from the blood, hemoconcentration, drug addition, obtaining blood samples, heating and cooling of the blood, and the like.

During a surgical procedure using the heart/lung bypass machine system 100, various vital signs of the patient 10 are measured and/or monitored. For example, a patient mean arterial pressure ("MAP") may be measured. The MAP of the patient 10 is a parameter that a perfusionist operating the heart/lung bypass machine system 100 will monitor in order to ensure that the heart/lung bypass machine system 100 is functioning as desired during the surgical procedure. In some cases, the MAP reading is displayed on a screen of an anesthesia system, and/or displayed on the operating room screen. If the MAP of the patient 10 is outside of a desired range, the perfusionist may make adjustments to the heart/lung bypass machine system 100 to improve the MAP of the patient 10.

The heart/lung bypass machine system 100 also includes the heart/lung machine 110. The heart/lung machine 110 is a complex system that includes multiple pumps, monitors, controls, user interfaces, alarms, safety devices, and the like, that are all monitored and operated/adjusted by the perfusionist during a surgical procedure. For example, the depicted heart/lung machine 110 includes an arterial pump 111 (which can be a drive system for a disposable centrifugal pump 124 as shown, or a peristaltic pump), a suction pump 112, a vent/drainage pump 113, a cardioplegia solution pump 114, and a cardioplegia delivery pump 115. The heart/lung machine 110 can also include, or be interfaced with, devices such as a tubing occluder, gas blender, and the like. The parameters of the heart/lung machine 110, such as the rotational speed and other parameters of each of the pumps, are set and adjusted by the perfusionist. For example, the speed of the arterial pump 111 is adjusted to maintain a desirable level of blood in the reservoir 123, and to provide a requisite level of blood circulation within the patient 10.

The heart/lung bypass machine system 100 also includes one or more temperature control systems 130. In a first aspect, the temperature control system(s) 130 is/are used to heat and cool the patient's blood in the oxygenator 125 via a heat exchanger. Additionally, the temperature control system(s) 130 is/are used to heat and cool the cardioplegia solution being delivered to the heart 12 of the patient 10. In general, the temperature control system(s) 130 is/are used in cooling modes during the procedure (to reduce metabolic demands), and subsequently used to warm the blood and/or cardioplegia solution when the surgical procedure is nearing its end. The perfusionist is tasked with monitoring and adjusting the temperature control system(s) 130 as needed during the surgical procedure.

The heart/lung bypass machine system 100, as depicted, also includes the blood monitoring system 140. The blood monitoring system 140 is used to monitor the extracorporeal blood of the patient 10 during the surgical procedure. Parameters being monitored can include, but are not limited to, pH, $pCO_2$, $pO_2$, K+, temperature, $SO_2$, hematocrit, hemoglobin, base excess, bicarbonate, oxygen consumption and oxygen delivery. The perfusionist is tasked with monitoring the blood monitoring system 140 during the surgical procedure. In some cases, the perfusionist will need to adjust other components or subsystems of the heart/lung bypass machine system 100 in response to readings from the blood monitoring system 140.

The heart/lung bypass machine system 100, as depicted, also includes the perfusion data management system 150 and the regional oximetry system 160. These systems can also be used by the perfusionist to monitor the status of the patient 10 and/or the status of the heart/lung bypass machine system 100 during surgical procedures.

From the above description, it can be observed and understood that the perfusionist is tasked with a vast amount of very important responsibilities during a surgical procedure using the heart/lung bypass machine system 100.

Figure 2:
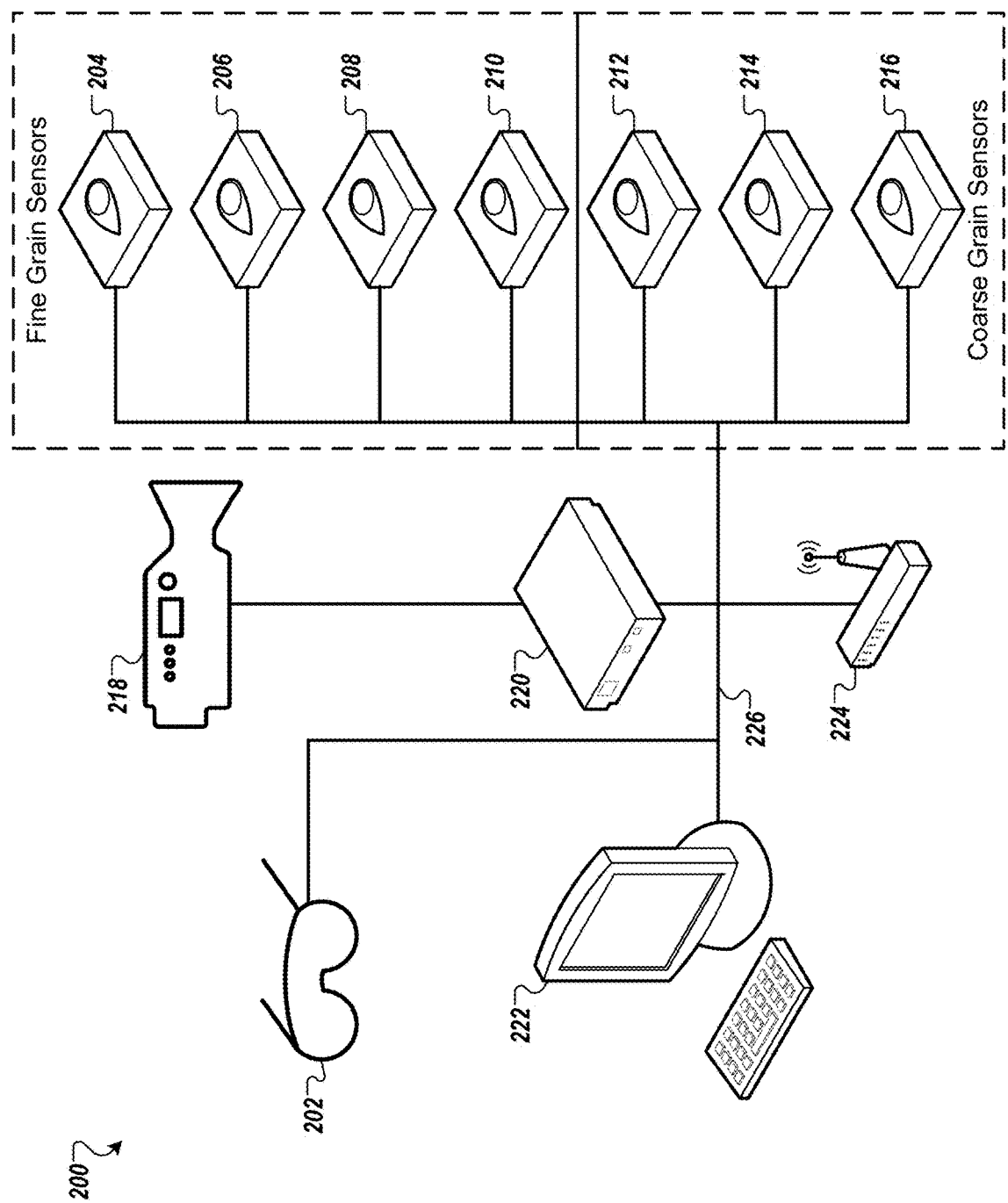
FIG. 2 is a schematic diagram of example monitoring and display hardware useful for providing heart-lung-machine sensor data in augmented reality.

Referring to FIG. 2, hardware 200 is used to monitor the operation of a heart-lung machine, such as that described with reference to FIG. 1. The hardware 200 includes a head-worn augmented-reality display 202, sometimes also referred to as "smart glass" or "smart glasses", among other names. For example, the display 202 can take the form of a pair of glasses, a visor, an open area, or a face-shield that a user (e.g., a perfusionist) wears on their head or face. The display 202 includes a viewfield through which a user can view physical objects in their field of view, which is sometimes referred to as "non-occluded" or a "non-occluded heads-up display (HUD)", among other names. For example, the display 202 can include a clear portion of glass, plastic, or similar transparent material through which light emitted from physical objects passes into the user's eye. In another example, the display 202 may be a solid, opaque device that completely or partially occludes the user's view, sometimes referred to as "occluded" or an "occluded HUD", among other names. In such a case, the viewfield can include one or more screens (e.g., Light Emitting Diode or LED screens) along with one or more cameras that capture a video data of the user's point-of-view. Video is then rendered on the screens, providing the user with a viewfield that is similar to a clear view of the physical environment, possibly imperceptibly similar.

In yet another example, the display 202 can include a retinal projector configured to project an image directly onto the wearer's eye or eyes. In some cases, a display 202 with retinal projector can include a clear portion of glass, plastic, or similar transparent material through which light emitted from physical objects passes into the user's eye. In some cases, a display 202 with retinal projector can include one or more cameras that capture a video data of the user's point-of-view. Video is then rendered and projected onto the user's eye, or eyes, providing the user with a viewfield that is similar to a clear view of the physical environment, possibly imperceptibly similar. In some implementations, the display 202 can be configured to account for seeing difficulties of the user. For example, a retinal projector can be configured to provide a projection to a user with a cloudy cornea or cataracts in a way that is clear to such a user.

In yet another example, the display 202 can include a half-mirrored portion of glass, plastic, or similar transparent material through which light emitted from physical objects passes into the user's eye, while light is emitted onto the half-mirror view field to render glyphs etc.

The display 202 is configured to render glyphs and to render video in the viewfield. For example, light emitters can emit light into a transparent viewfield so that the user is shown a reflection of the light. In another example, where screens are used to show video from the user's point-of-view, the glyphs and video can be shown superimposed over the point-of-view video. In any case, the display 202 shows a presentation of the glyphs and the video as an overlay to the view of the physical objects.

The display 202 can include other features as well. For example, a microphone and earphone may be included in the display 202 to connect to an intercom, cellular phone, or other telecommunication device. This can allow the operator to communicate, via the microphone and earphone, with people in the same facility or more distant.

Sensors 204-216 sense parameters of the operation of a heart-lung machine (see FIG. 1). As will be appreciated, a variety of different sensors may be used depending on the particular configuration of the heart-lung machine. For example, pressure sensors may be used to sense pressure in tubes of the extracorporeal circuit, thermocouples may be used to sense operating pressures, reservoir levels may be monitored via ultrasonic sensors or strain gages, blood parameters of the subject may be monitored with a multi-function blood parameter monitoring device, electrical impedance sensors, light sensors, etc. Other possible sensors include battery-charge sensors, proximity sensors, vibration sensors, gyroscopic sensors, blood sensors capable of sensing DO2, VO2, Hgb and hematocrit, etc.

Each of the sensors 204-216 is exposed to phenomena of the environment in or around the heart-lung machine and generates an electrical signal based on that phenomenon. These electrical signals may be digital signal, analog signals, or a mix of the two. Appropriate circuity may be used to smooth, normalize, and filter these signals as is needed. While some sensors 204-210 are shown here as "fine grain sensors" and some 212-216 are shown as "coarse grain sensors", this may or not be reflected in the physical makeup or electrical signals of the sensors. As will be understood, subsampling, supersampling, interpolation, and averaging processes can be used to manipulate the operation of sensors. In fact, some particular sensors may be used as both fine grain and coarse grain at the same time or at different times.

An optional video sensor 218 captures video of the operation of the heart-lung machine. For example, the video sensor 218 can include a photo-reactive sensor panel (e.g., a charged coupled device (CCD) or complementary metal-oxide-semiconductor (CMOS) panel). The video sensor 218 may also include an illumination source, a physical shutter, a flexible mounting so the point-of-view can be adjusted, etc.

A controller 220 includes a hardware processor and computer memory. For example, the computer memory may store, in either a read-only or in a read-write format, a series of instructions for the processor to perform. These instructions can include software, firmware, drivers, data files, etc. used in the operation of the controller.

A terminal 222 can include any sort of display, including those that are not head-worn. The can include a stand-alone display optionally having input devices such as keyboard, mouse, trackball, or touchpad, can include a display worn on the arm, wrist, or shoulder, etc. The terminal 222 can provide the user with a relatively stationary or mobile access point for input and output activities. Terminal 222 or elements thereof may be movable such as by being mounted on a swing arm, on a sliding drawer, on a user, etc., including being mounted on a heart-lung machine.

A network interface 224 can communicate with external network locations. For example, the network interface 224 can provide access to local area networks, to the Internet, or to other peripheral devices. Elements of the hardware 200 can use the network interface 224 to communicate with other elements of the hardware 200 or with other remote destinations.

A data network 226 communicably couples the elements of the hardware 200. As will be understood, the data network 226 can include one or more logical network and one or more physical medium for data exchange. For example, an Ethernet network may connect the sensors 204-216, the video sensor 218, and the controller 220 while a wireless (e.g., WiFi or BlueTooth) network connects the controller 220 and the display 202.

The controller 220 can receive, through the data network 226, data from the sensors 204-216 and the video sensor 218. For example, the sensor 204 can be a pressure sensor that continuously reads pressure in a line as the heart-lung machine operates. The sensor 204 can report a first parameter (e.g., a four-digit real number of the sensed pressure in mm/Hg) to the controller 220. The controller 220 can then use this as a fine-grain parameter and send, to the display 202, instructions to show as a glyph an alpha-numeric value (e.g., a character string of the four-digit real number and "mm/Hg") based on the first parameter of the operation of the heart-lung machine.

The sensor 216 can be a fluid level sensor that returns "True" if fluid, likely blood, in the reservoir of the extracorporeal circuit is greater than a given volume. For example, the sensor 216 can be mounted in or on an exterior of the reservoir and, if there is sufficient blood to cover the sensor 216, the sensor 216 sends a value of "True" as a second parameter to the controller 220 and a value of "False" if there is not sufficient blood to cover the sensor 216. Alternatively, in some cases the sensor 216 can be an ultrasonic level sensor that does not contact the blood. The controller 220, upon receipt of a "True" value, can send to the display 202 instructions to show a graphic of a reservoir with a green background, which can indicate that there is sufficient blood in the reservoir. Later, the controller can receive a "False" value and can then send the display 202 instructions to show a graphic of a reservoir with a red background, which can indicate that there is insufficient blood in the reservoir, or nearly so. In some cases, two or more of the sensors 216 can be used to sense the fluid levels in the reservoir. For example, without limitation, a first sensor 216 can be positioned at a level that would result in sending an alert message if the level of the fluid is below the position of the first sensor 216. A second sensor 216 can be positioned lower than the first sensor 216 at a level that would result in stopping the arterial pump of the heart-lung machine to avoid the ingress of air into the extracorporeal circuit that could result if the reservoir becomes empty of fluid. As will be appreciated, these graphics may be stored by the processor 220 before operation of the heart-lung machine and may be selected to quickly transmit semantic information to a user (e.g., yellow being a cautionary alert indicating a worsening condition, green being good, red or blinking/flashing red being bad).

In some embodiments, the optional video sensor 218 can be fixed to point at the same reservoir as is being sensed by the sensor 216. The video sensor 218 can send to the controller 220 video data of the reservoir. The controller 220 can send to the display 202 instructions to show a video based on the video data received from the video sensor 218.

In some implementations, the information gathered by the sensor 216 and/or the video sensor 218 may be used to generate other values. For example, in addition to being used to sense present the level of blood as a value, the controller 220 can also identify when the value of the level is changing (e.g., increasing or decreasing), and can identify the speed of such a change. The increasing or decreasing can be shown in the form of an alphanumerical character, a glyph (e.g., an up arrow and a down arrow), a color (e.g., red/green or yellow/blue). The speed of change can be shown separately from the indication of change (e.g., with an exclamation mark next to the change indication) or by altering the change indication (e.g., causing a blink or a change in size).

In some implementations, the video sensor 218 can be tasked to sense one or more different phenomena. For example, in some implementations the video sensor 218 may be tasked to record an alphanumerical output of, for example, a meter or display. For example, a piece of equipment may produce a human-readable output that includes alphanumerical characters, but that does not have data network capabilities. In such a case, the video sensor 218 can record the alphanumerical output, and the controller 220 can generate, from the recording, a corresponding computer-readable value. In some embodiments, two or more of the video sensors 218 can be included as components of the hardware 200. For example, in some embodiments, a first video sensor 218 can be used to monitor the reservoir and one or more additional video sensors 218 can be used to monitor meters and/or displays. In some embodiments, the system of hardware 200 includes no video sensor 218 to monitor the reservoir. Instead, one or more level sensors (e.g., sensor(s) 216) alone can be used to detect the level of fluid in the reservoir. In some embodiments, no video sensor 218 is included whatsoever (while the hardware 200 can include the other components, e.g., sensors 204-216). It should be understood that the system of hardware 200 is flexible and expandable such that it can be configured and adapted to the needs of particular users (e.g., perfusionists).

In some implementations, the information gathered by the video sensor 218 may be used to generate other values. For example, in addition to being used to record alphanumerical output, the controller 202 can also identify when the value of the alphanumeric output is changing (e.g., increasing or decreasing), and can identify the speed of such a change. The increasing or decreasing value can be shown in the form of an alphanumerical character, a glyph (e.g., an up arrow and a down arrow), a color (e.g. red/green or yellow/blue), and the like. The speed of change of the value can be shown separately from the indication of change (e.g., with an exclamation mark next to the change indication) or by altering the change indication (e.g., causing a blink or a change in size).

As can now be appreciated, both the sensor 216 and the video sensor 218 can be used to sense the same or related phenomena—in this case the blood level within the reservoir of the extracorporeal circuit that is coupled to the heart-lung machine. The sensor 216 in this example is only able to provide an indication of if there is more or less blood in the reservoir than a particular, possibly fixed, level. However, a perfusionist may benefit from access to greater information than only that single indication. As such, the presentation of video of the reservoir in the display 202 can provide uninterrupted information about the level of blood with only a simple physical and/or mental concentration on a portion of the augmented-reality presentation. However, if the perfusionist is concentrating on another task, it may be difficult for them to also give full attention to the video. As such, a highly visible glyph, in the form of a graphic that appears to turn from green to red, and grab attention of the perfusionist to indicate that the perfusionist should pay attention to the reservoir video.

As can be appreciated, such a configuration can benefit hardware 200 where fine-grain sensing would be beneficial, but is technologically problematic. In some heart-lung machines, accurate measures of fluid levels in a reservoir become complicated or impossible due to material selection, the interplay of currents when fluid is both being added and removed from the reservoir at different rates, environmental interference, etc. However, the hardware 200 can be utilized to take advantage of the fact a video of the reservoir provides more-than-sufficient information to quickly understand the state of the reservoir. Similarly, the hardware 200 can be advantageously used by a perfusionist as an add-on to an existing heart-lung machine that was not provided with the hardware 200. That is, the manufacturer of the heart-lung machine may only provide some of the sensors 204-216, and the perfusionist may want or need more data than what is provided. In such a case, the perfusionist (or a technician on their behalf) can modify the heart-lung machine with the hardware 200 to provide greater functionality on an old or feature-poor heart-lung machine.

In some cases, the hardware 200 may be developed as an integral part of a heart-lung machine. That is, the elements of a heart-lung machine may include housings, brackets, and chambers that include, e.g., the sensors 204-216. In some cases, the hardware 200 may be made available as an optional upgrade to a heart-lung machine by the vendor or manufacturer of the heart-lung machine. That is, the designer of a heart-lung machine may design the heart-lung machine so that some or all of the hardware 200 are available as optional add-on components that may, or may not, be purchased with the heart-lung machine. In some cases, the hardware 200 may be made available as an after-market add-on system. That is, the hardware may be sold to an owner that already owns a heart-lung machine that was made by a manufacturer different from the manufacturer of the hardware 200. Other distribution options are also possible.

One beneficial feature of the system 200 is that various elements of the system 200 may be geographically separated and/or multiple copies of some components may be provided. For example, the sensors 204-2016 may be located in one location (e.g., a hospital on one country) with one display 202 worn by a clinician at that location, while a second display 202 may be located in another location (e.g., a training center in another country) worn by another user. In such a case, both users may be presented with the same views, or with different views depending on context. One use case for such a configuration is a training use case. A trainer in one physical location can "virtually sit-in" on a procedure being performed by the clinician that is, geographically speaking, far way. With remote communication (e.g., telephone, video conference), the trainer may assist the clinician in a real procedure or in a simulated teaching-procedure. For example, the trainer can help the clinician learn how to use the technology, how to perform a particular procedure, etc. This may be of particular value in, for example, procedures with patients with very rare or complex conditions.

Consider a patient with a very rare condition, for which there is only one clinician in the world with deep expertise and experience. If that patient is undergoing a procedure in a different location than the expert, a local clinician can collaborate with the remote expert. The local clinician can physically interact with the patient and heart-lung machine, all the while receiving the unique input and guidance that the expert can provide when given up-to-the-moment information by the system 200.

Further, new clinicians can be trained in the use of the heart-lung machine by a trainer without requiring the trainer and the new clinician to be in the same location. This can beneficially allow the trainers remain in a central training-hub and train, in the same day, new clinicians that are so far apart from each other the trainer could never travel from one to the next in the same day.

Similarly, an expert clinician can share the system 200 with new clinicians so that the new clinicians can observe the way that an expert clinician performs procedures. In addition to the advantages below, the system 200 can include many remote displays 202 (or terminals 222) so that many new clinicians can be educated at the same time. And, this can include many new clinicians that are geographically separated.

The system 200 can also be used for diagnostic, troubleshooting, and technical support purposes. For example, a technician installing a new component in a heart-lung machine may connect with a remote technical expert that can guide them through the installation process, troubleshoot an installation error, etc.

As will be appreciated, these and other use cases can be provided without requiring the time, expense, and hassle of travel. Furthermore, because the system 200 can share the point-of-view of one user with other users, communications that could never happen even in person can be made. For example, an expert clinician can, in real time, spot that a new clinician is spending too much time with their attention focused on one reading, while they should be paying more attention to another aspect of the perfusion system. This kind of learning and observation can advantageously improve clinical outcomes, training, and service operations of the system 200 and the associated medical technologies.

Figure 3:
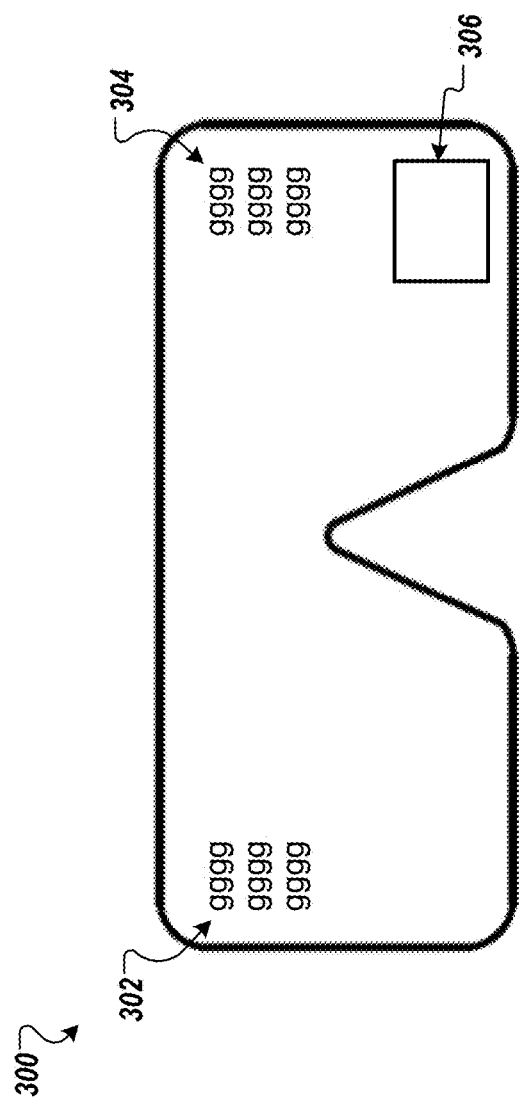
FIGS. 3-5 are schematic diagrams of example augmented-reality presentations.

Referring to FIG. 3, a schematic diagram 300 of an example augmented reality presentation is shown. In this example, the presentation is configured for a visor or goggles that provide a generally rectangular area, with a portion removed where the user's nose will generally be present. Glyph areas 302 and 304, represented by recurring "g" characters, are areas of the presentation where the display device is configured to present one or more glyphs. Video area 306 is an area of the presentation where the display device is configured to present one or more videos. It will be appreciated that the number, shape, size, and location of areas can vary from presentation to presentation, and can be constrained by the technical limitations of the display device being used.

Figure 4:
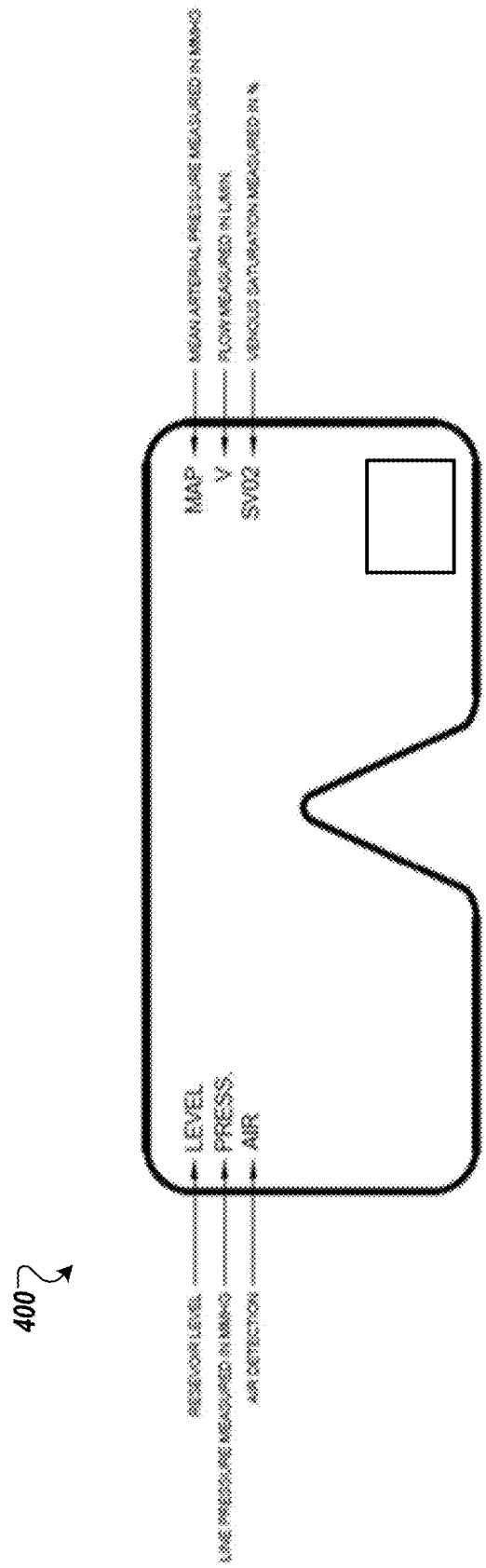

Referring to FIG. 4, a schematic diagram 400 of an example augmented reality presentation is shown. In this example, the glyph areas are populated with fields for possible glyphs related to reservoir level, line pressure, air detection, mean arterial pressure, flow volume, and venous saturation mean.

Figure 5:
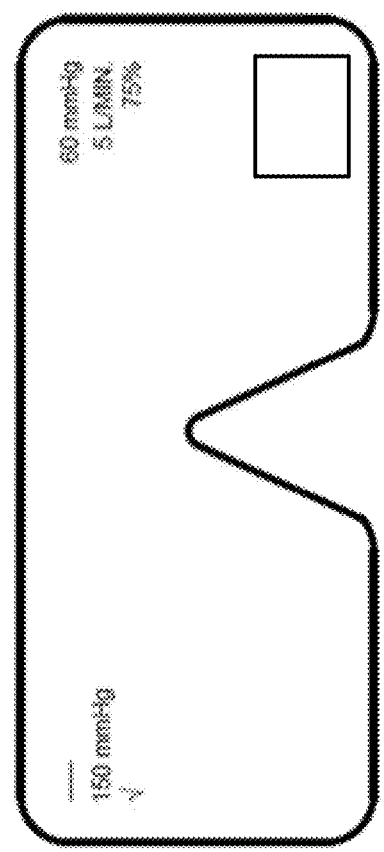

Referring to FIG. 5, a schematic diagram 500 of an example augmented reality presentation is shown. In this example, a graphic is populated into the fields for reservoir level and air detection, while alphanumeric values are populated into the remaining glyph areas.

The augmented reality presentations can be configured to show data in ranged expected for human or other patient ranges. For example, a range of values as described here may be used:

MAP: 0 to 400 mmHg or completely off on range settings;
FLOW: 0 to 10 L/min or complete off on ranges settings;
VENOUS SAT: 0 to 100% or off; and
LINE PRESSURE: 0 to 500 mmHg or off.
For example as smaller woman of 60 kg:
MAP: normal may be approx. 60 mmHg with range setting of 55 mmHg on low alarm and 80 mmHg on high alarm;
FLOW: normal 4 L/min with a setting of 3 L/min on low alarm and 5 L/min on high alarm;
VENOUS SAT: 80% normal with a low setting of 65% and a high setting of 90%; and
LINE PRESSURE: 180 mmHg with a low setting of 90 mmHg and a high setting of 250 mmHg.
For example a larger man of 100 kg:
MAP: normal may be approx. 75 mmHg with a range setting on low alarm of 60 mmHg and 90 mmHg on high alarm;
FLOW: normal 6 L/min with a setting of 3.5 L/min on low alarm and 7.5 L/min on high alarm;
VENOUS SAT 70% with a low setting of 60% and a high setting of 80%; and
LINE PRESSURE: 240 mmHg with a low setting of 100 mmHg and a high setting of 350 mmHg.

Figure 6:
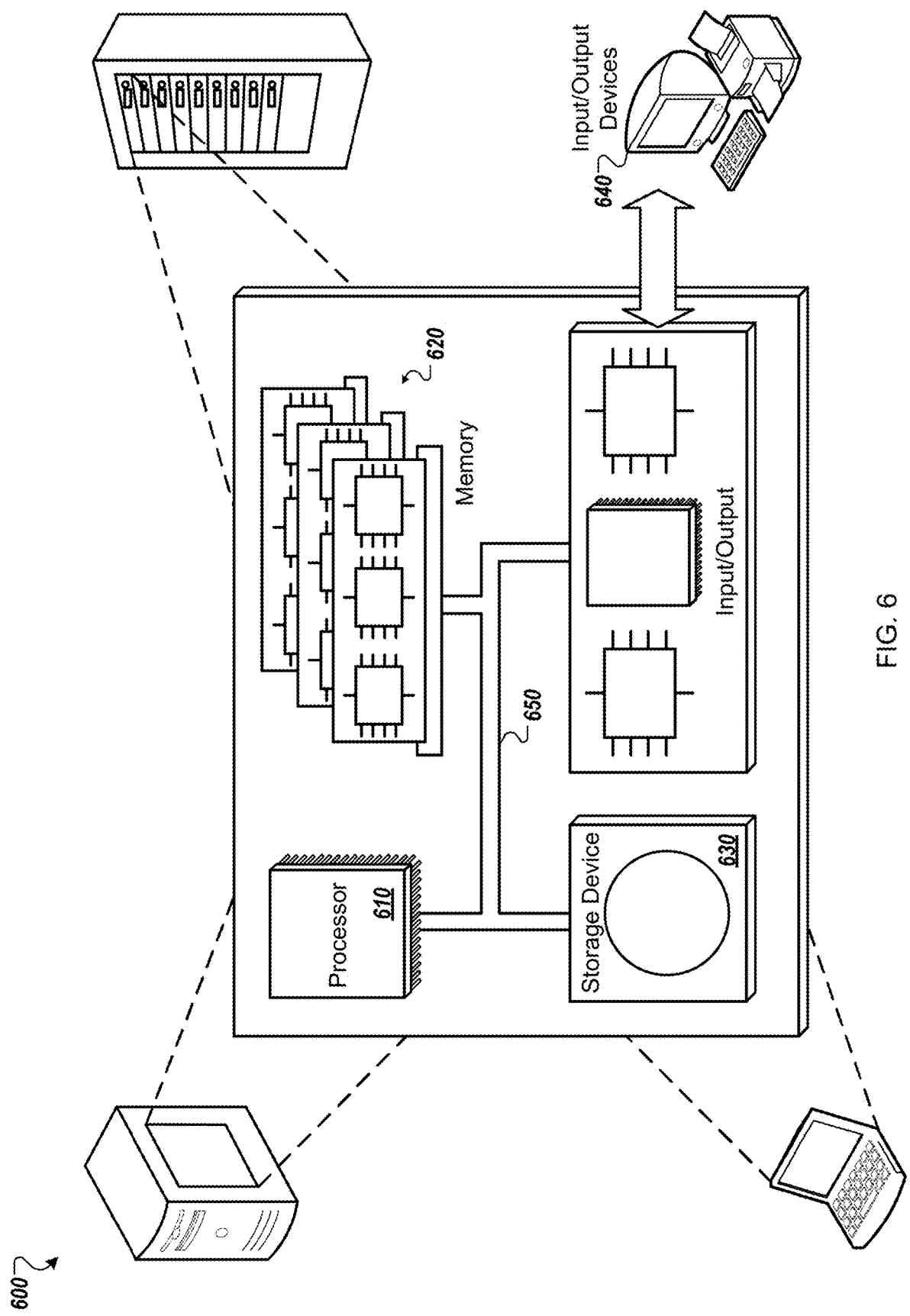
FIG. 6 is a block diagram of an example data processing apparatus.

Referring to FIG. 6, a block diagram of an example data processing apparatus 600 is shown. The system 600 includes a processor 610, a memory 620, a storage device 630, and an input/output device 640. Each of the components 610, 620, 630, and 640 can, for example, be interconnected using a system bus 650. The processor 610 is capable of processing instructions for execution within the system 600. In one implementation, the processor 610 is a single-threaded processor. In another implementation, the processor 610 is a multi-threaded processor. The processor 610 is capable of processing instructions stored in the memory 620 or on the storage device 630.

The memory 620 stores information within the system 600. In one implementation, the memory 620 is a computer-readable medium. In one implementation, the memory 620 is a volatile memory unit. In another implementation, the memory 620 is a non-volatile memory unit.

The storage device 630 is capable of providing mass storage for the system 600. In one implementation, the storage device 630 is a computer-readable medium. In various different implementations, the storage device 630 can, for example, include a hard disk device, an optical disk device, or some other large capacity storage device.

The input/output device 640 provides input/output operations for the system 600. In one implementation, the input/output device 640 can include one or more network interface devices, e.g., an Ethernet card, a serial communication device, e.g., an RS-232 port, and/or a wireless interface device, e.g., an 802.11 card. In another implementation, the input/output device can include driver devices configured to receive input data and send output data to other input/output devices, e.g., keyboard, printer and display devices 660. Other implementations, however, can also be used, such as mobile computing devices, mobile communication devices, set-top box television client devices, etc.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both.

The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a user computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A system for displaying heart-lung machine sensor data in augmented reality, the system comprising:
    a head-worn augmented-reality display comprising a viewfield through which a user of the augmented-reality display can view physical objects in their field of view, the augmented-reality display configured to render glyphs and to render video in the viewfield such that, as the user views physical objects in their field of view, the user is shown a display of the glyphs and the video as an overlay to the view of the physical objects;
    a heart-lung machine configured to engage in an operation to provide a patient with an extracorporeal blood flow circuit;
    at least one fine-grain sensor configured to sense a first parameter of the operation of the heart-lung machine;
    a plurality of level-sensors configured to each sense level-parameters for fluid that flows into a reservoir during operation of the heart-lung machine relative to a corresponding, predefined level, each level-sensor's corresponding, predefined level being different from the other level-sensors' corresponding, predefined levels;
    at least one video sensor to capture video data of the reservoir during operation of the heart-lung machine;
    a controller comprising a hardware processor and computer memory; and
    a data-network that communicably couples at least the fine-grain sensor and the plurality of level-sensors to the controller and further couples at least the controller to the head-worn augmented-reality display;
    wherein the controller is configured to:
        receive, through the data-network, the first parameter of the operation of the heart-lung machine;
        receive, through the data-network, the level-parameters;
        receive, through the data-network, the video data of the reservoir during the operation of the heart-lung machine;
        send, to the augmented-reality display, instructions to show as a glyph an alpha-numeric value based on the first parameter of the operation of the heart-lung machine;
        send, to the augmented-reality display, instructions to show as a glyph, selected graphic from a plurality of possible graphics based on the level-parameters; and
        send, to the augmented-reality display, instructions to show a video based on the video data.

2. The system of claim 1, wherein:
    the fine-grain sensor is a line pressure sensor configured to sense a pressure in a line of a heart-lung machine.

3. The system of claim 1, wherein:
    the fine-grain sensor is an air detection sensor configured to sense a presence of air in a line of a heart-lung machine.

4. The system of claim 1, wherein:
    the fine-grain sensor is an arterial pressure sensor configured to sense a mean arterial pressure of a heart-lung machine.

5. The system of claim 1, wherein:
    the fine-grain sensor is a flow volume sensor configured to sense a flow volume of a heart-lung machine.

6. The system of claim 1, wherein:
    the fine-grain sensor is a venous saturation sensor configured to sense a mean venous saturation of a heart-lung machine.

7. The system of claim 1, wherein, the plurality of possible graphics includes an altered-graphic that corresponds to the selected graphic and differs from the selected graphic in at least a color, wherein the color is a red color;
    the controller is configured to send the selected graphic when at least one of the level-parameters is within a normal range and to send the altered graphic when the at least one of the level-parameters is outside of a normal range; and
    the controller is configured to send the selected graphic at a first time and to send the altered graphic at a second time later than the first time.

8. The system of claim 1, wherein:
    the system further comprising a stand-alone monitor; and
    the controller is further configured to send, to the stand-alone monitor, instructions to show monitor-data on the stand-alone monitor, at least some of the monitor-data including one of the group consisting of the alpha-numeric value, the selected graphic, and the video.

9. The system of claim 1, wherein the video sensor records an alphanumerical display; and
    wherein the controller is further configured to:
        generate a corresponding computer-readable value;
        send, to the augmented-reality display, instructions to show the corresponding computer-readable value;
        determine a change to the corresponding computer-readable value; and
        send, to the augmented-reality display, instructions to show the change to the corresponding computer-readable value.

10. The system of claim 1, wherein the controller is further configured to:
    determine a change to the level-parameters; and send, to the augmented-reality display, instructions to show as a second glyph based on the change of the level-parameters.

11. The system of claim 1, wherein the augmented-reality display comprises light emitters configured to emit light into a transparent viewfield to render the glyphs.

12. The system of claim 1, wherein the augmented-reality display comprises light emitters configured to emit light into a half mirror viewfield to render the glyphs.

13. The system of claim 1, wherein the augmented-reality display comprises one or more screens configured to display video to render the glyphs.

14. The system of claim 1, wherein the augmented-reality display comprises a retinal projector configured to project an image onto one or more eyes of the user to render the glyphs.

15. A controller device for showing heart-lung-machine sensor data in augmented reality, the controller comprising a hardware processor and computer memory, the controller configured to:
receive, through a data-network, a first parameter of an operation of the heart-lung machine;
receive, through the data-network, a plurality of level-parameters sensed by a corresponding plurality of level-sensors configured to each sense at least one of the level-parameters for fluid that flows into a reservoir during operation of the heart-lung machine relative to a corresponding, predefined level, each level-sensor's corresponding, predefined level being different from the other level-sensors' corresponding, predefined levels;
send, to an augmented-reality display, instructions to show as a glyph an alpha-numeric value based on the first parameter of the operation of the heart-lung machine;
send, to the augmented-reality display, instructions to show as a glyph, a selected graphic from a plurality of possible graphics based on the level-parameters;
receive, through the data-network, video data of the operation of the heart-lung machine; and
send, to the augmented-reality display, instructions to show a video based on the video data.

16. The controller device claim 15, wherein the video sensor records an alphanumerical display; and
wherein the controller is further configured to:
generate a corresponding computer-readable value; and
send, to the augmented-reality display, instructions to show the corresponding computer-readable value.

17. The controller of claim 15, wherein the controller is further configured to:
determine a change to the corresponding computer-readable value; and
send, to the augmented-reality display, instructions to show the change to the corresponding computer-readable value.

18. The controller device of claim 15, wherein the controller is further configured to:
determine a change to the level-parameters; and
send, to the augmented-reality display, instructions to show as a second glyph based on the change of the second parameter.

19. A system for displaying heart-lung machine sensor data in augmented reality, the system comprising:
a head-worn augmented-reality display comprising a viewfield through which a user of the augmented-reality display can view physical objects in their field of view, the augmented-reality display configured to render glyphs in the viewfield such that, as the user views physical objects in their field of view, the user is shown a display of the glyphs as an overlay to the view of the physical objects;
a heart-lung machine configured to engage in an operation to provide a patient with an extracorporeal blood flow circuit;
at least one fine-grain sensor configured to sense a first parameter of the operation of the heart-lung machine;
a plurality of level-sensors configured to each sense level-parameters for fluid that flows into a reservoir during operation of the heart-lung machine relative to a corresponding, predefined level, each level-sensor's corresponding, predefined level being different from the other level-sensors' corresponding, predefined levels;
means for capturing video data of the reservoir during operation of the heart-lung machine;
a controller comprising a hardware processor and computer memory; and
a data-network that communicably couples at least the fine-grain sensor and the coarse-grain sensor to the controller and further couples at least the controller to the head-worn augmented-reality display;
wherein the controller is configured to:
receive, through the data-network, the first parameter of the operation of the heart-lung machine;
receive, through the data-network, the second parameter of the operation of the heart-lung machine;
receive, through the data-network, the video data of the reservoir during the operation of the heart-lung machine;
send, to the augmented-reality display, instructions to show as a glyph an alpha-numeric value based on the first parameter of the operation of the heart-lung machine; and
send, to the augmented-reality display, instructions to show as a glyph, selected graphic from a plurality of possible graphics based on the level-parameters.

* * * * *

UNITED STATES PATENT AND TRADEMARK OFFICE
CERTIFICATE OF CORRECTION

| | |
|---|---|
| PATENT NO. | : 11,583,347 B2 |
| APPLICATION NO. | : 17/085765 |
| DATED | : February 21, 2023 |
| INVENTOR(S) | : Joseph Geric and Takeshi Tsubouchi |

It is certified that error appears in the above-identified patent and that said Letters Patent is hereby corrected as shown below:

In the Claims

In Column 19, Line 42, In Claim 16, after "device" insert -- of --.

Signed and Sealed this
Fourteenth Day of November, 2023

Katherine Kelly Vidal
*Director of the United States Patent and Trademark Office*